United States Patent [19]

Jassawalla

[11] 4,199,307
[45] Apr. 22, 1980

[54] MEDICAL INFUSION SYSTEM

[75] Inventor: Jal S. Jassawalla, San Francisco, Calif.

[73] Assignee: Andros Incorporated, Berkeley, Calif.

[21] Appl. No.: 878,700

[22] Filed: Feb. 17, 1978

Related U.S. Application Data

[63] Continuation-in-part of Ser. No. 812,904, Jul. 5, 1977, abandoned.

[51] Int. Cl.² .................. F04B 43/08; F04B 45/06
[52] U.S. Cl. .................. 417/474; 128/214 F; 128/DIG. 12; 417/478; 417/479; 417/480
[58] Field of Search .............. 417/474, 478–480, 417/412; 128/214 F, DIG. 12, DIG. 3, 214.2

[56] References Cited

U.S. PATENT DOCUMENTS

| | | | |
|---|---|---|---|
| 2,105,200 | 1/1938 | Phelps | 417/474 |
| 2,351,828 | 6/1944 | Marsh | 417/474 X |
| 2,393,838 | 1/1946 | Tarbox | 417/474 |
| 2,412,397 | 12/1946 | Harper | 417/474 |
| 2,625,932 | 1/1953 | Salisbury | 128/214.2 |
| 3,039,399 | 6/1962 | Everett | 128/DIG. 3 |
| 3,737,251 | 6/1973 | Berman et al. | 417/12 |
| 3,778,195 | 12/1973 | Bamberg | 417/474 |
| 4,126,132 | 11/1978 | Portner et al. | 128/214 F |

FOREIGN PATENT DOCUMENTS

| | | | |
|---|---|---|---|
| 800805 | 12/1950 | Fed. Rep. of Germany | 417/478 |
| 2300576 | 10/1976 | France | 128/214 F |

*Primary Examiner*—Dalton L. Truluck
*Attorney, Agent, or Firm*—Fitch, Even & Tabin

[57] ABSTRACT

A medical infusion system is described employing a pump for conducting fluid or semi-solids from an upstream portion to a downstream portion of the system. The pump includes conduit means defining, in part, a removable cassette having a window therein and a diaphragm spanning the window. The cassette has inlet and outlet openings valvelessly communicating with the pumping chamber or cavity of the cassette. Fluid in the conduit is pumped by restricting and opening the conduit means at three different locations, one of which is before the cassette and one of which is after the cassette and the third of which is at the diaphragm of the cassette.

3 Claims, 7 Drawing Figures

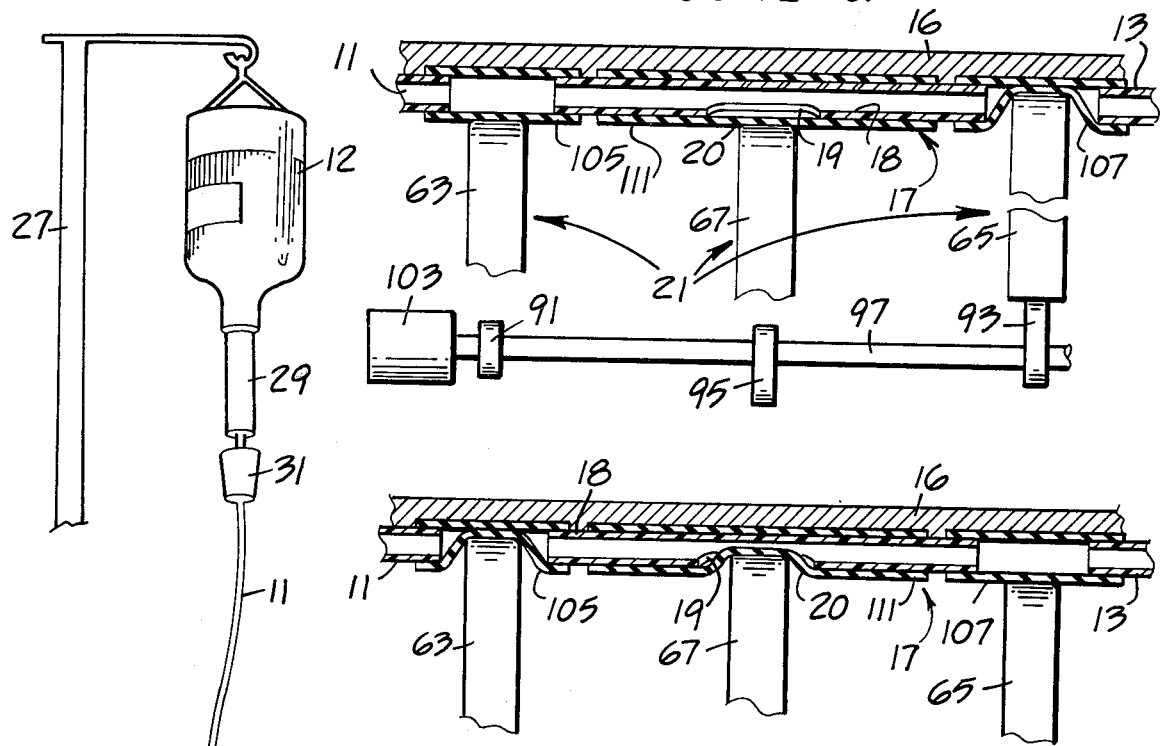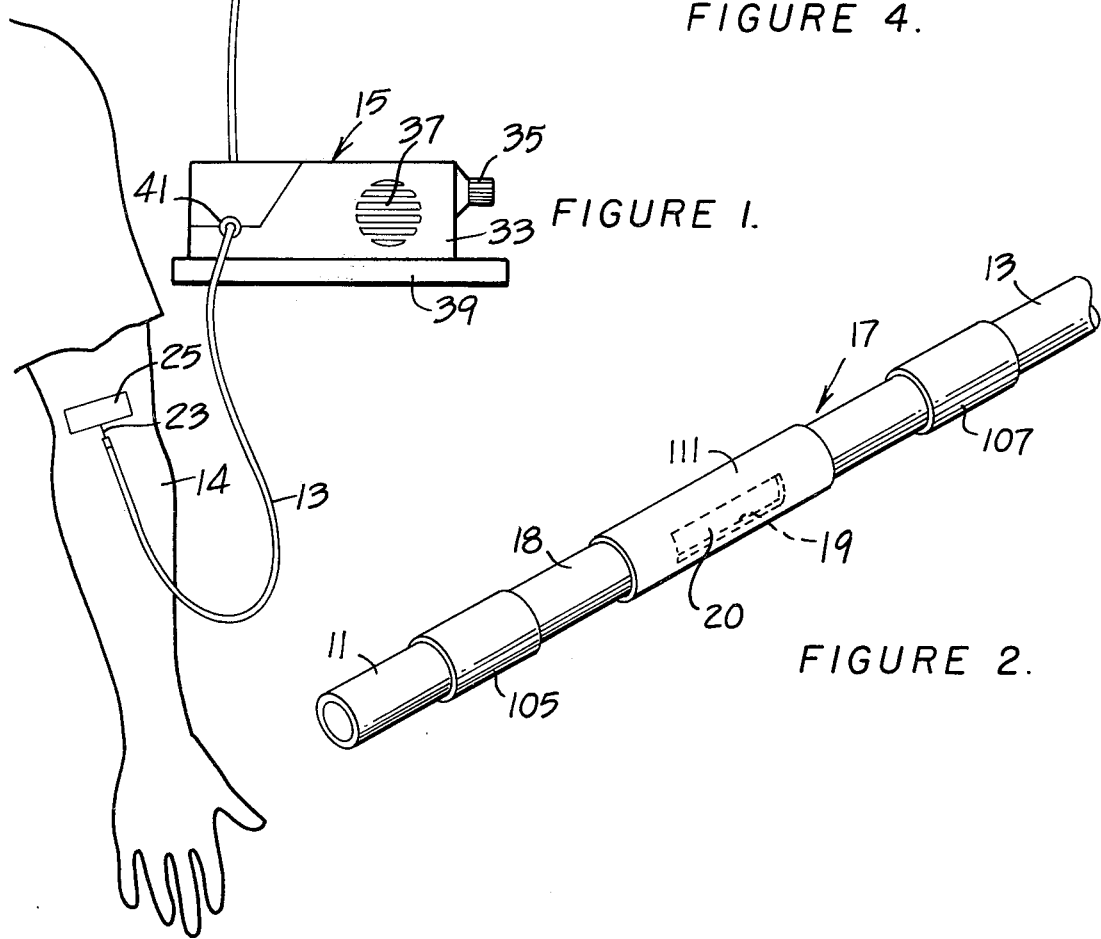

MEDICAL INFUSION SYSTEM

This application is a continuation-in-part of Application Ser. No. 812,904 filed July 5, 1977 and now abandoned. This invention relates to medical infusion systems and, more particularly, to an improved medical infusion system and to an improved pump and cassette for use therein.

Various medical infusion systems for the delivery of fluids or semi-solids into a patient are well known in the prior art, and such systems are in widespread daily use in hospitals throughout the world. These systems are commonly used for such things as the intravenous or intra arterial delivery of glucose solutions and blood plasma, for the delivery of drugs; and for enteral delivery of fluids and semi-solids. Typically, delivery is at controlled rates depending on the patient's needs, and in the case of drugs, the drug concentration being delivered is controlled.

A commonly used form of infusion system for intravenous delivery of fluids is comprised of a fluid container, a drip chamber and an adjustable clamp in the tube leading from the drip chamber to the needle penetrating the vein. The fluid container or bottle is supported at an elevated position with respect to the patient, with the drip chamber typically immediately thereunder. Transparent walls in the drip chamber coupled with a fixed volume of air therein allows the visual determination of the drip rate, which in turn is adjustable by the hose clamp. Thus, as fluid being delivered seeps past the pinched area of the hose, the air pressure in the drip chamber decreases, thereby encouraging the formation and dislodging of a drop from the tip of the small tube into the drip chamber coupled to the bottle. Such systems may be used alone, or the drip chamber used in conjunction with some other type of metering or pumping mechanism so that the visually observed drip rate may be used as a cross-check to verify the proper operation of the pumping device.

Another form of medical infusion system is the common medical syringe. Such a device, as is well known in the art, employs a hollow barrel in which the fluid to be injected is held. The contents of the barrel are discharged through a needle or catheter by a plunger which fits within the barrel and moves therein to reduce the internal volume of the barrel from its maximum to its minimum. Certain forms of automatic medical infusion apparatus employ the syringe type mode for displacing the fluid into the patient. Typically, however, such pumps are expensive, and are hard to control and refill.

Another type of system utilizes what is commonly referred to as a peristaltic pump. Such pumps are characterized by a length of flexible tubing which is disposed within an arc between a stator-like member and a rotor assembly. The rotor assembly is provided with a plurality of rollers which, upon rotation of the rotor assembly, successively pinch-off the tube and advance the location of the pinch-off so as to progressively advance the fluid within the tube along the tube at a rate determined by the rate of rotation of the rotor. Typically such systems are driven in rotation by some form of motor-gear assembly so as to provide the generally desired low pumping rate by the low speed rotation of the rotor. Such pumps have the advantage of having a disposable element in the fluid flow path, in that the length of tubing in the pump may be replaced after each use. In principle, the pumps also have the further advantage of providing low and variable flow rates by way of positive displacement of fluid. In practice, however, these systems characteristically exhibit poor accuracy and poor reproducibility. They also have the disadvantages of being mechanically complex, and require a substantial amount of power, thereby making them relatively expensive and difficult to use on battery operation.

Another form of pump utilizes a limited positive displacement by rapidly varying the volume of a pump chamber and employing inlet and outlet check valves. Such pumps have some advantages in that they may be specifically arranged so as to not pump air, thereby providing for automatic shut-off of the pump in the event of exhaustion of the supply of fluid being injected. Also such pumps may utilize a form of electromagnetic device allowing a pulse source to provide a variable pulse rate to thereby vary the pump rate. More importantly, however, such pumps may employ a replaceable cassette which forms the pump chamber or cavity and which may be replaced for each patient and type of fluid. Thus, sterility can be easily assured and cross contamination easily avoided.

Such pumps also have a number of disadvantages, however. In particular, the replaceable cassettes for such pumps are often relatively expensive and must be fabricated from a relatively large number of close tolerance parts. Aside from such elements as coil springs and close fitting moving parts for check valves, such pumps sometimes employ metal parts which must be protected against corrosion, etching, and other adverse effects thereon which may result in dissolved materials being infused.

Still another form of pump, somewhat akin to a peristaltic pump, is the type of pump wherein a conduit is restricted and opened in a sequence which produces the desired pumping action. Such a pump is shown and described in U.S. Pat. No. 2,105,200. Pumps of this type, however, have frequently not provided sufficient accuracy for many purposes, and are hard to control, clean and refill.

It is an object of the present invention to provide an improved medical infusion system.

Another object of the invention is to provide an improved pump for use in a medical infusion system.

A further object of the invention is to provide an improved cassette for use in a medical infusion system which is low in cost, relatively simple of operation, and of high reliability.

Other objects of the invention will become apparent to those skilled in the art from the following description taken in connection with the accompanying drawings wherein:

FIG. 1 is a schematic view of a medical infusion system constructed in accordance with the invention;

FIG. 2 is a schematic perspective view of a cassette and portions of the pump of the system of FIG. 1;

FIGS. 3 and 4 are schematic sectional views illustrating the operation of the pump portions of FIG. 2;

Figure 5:
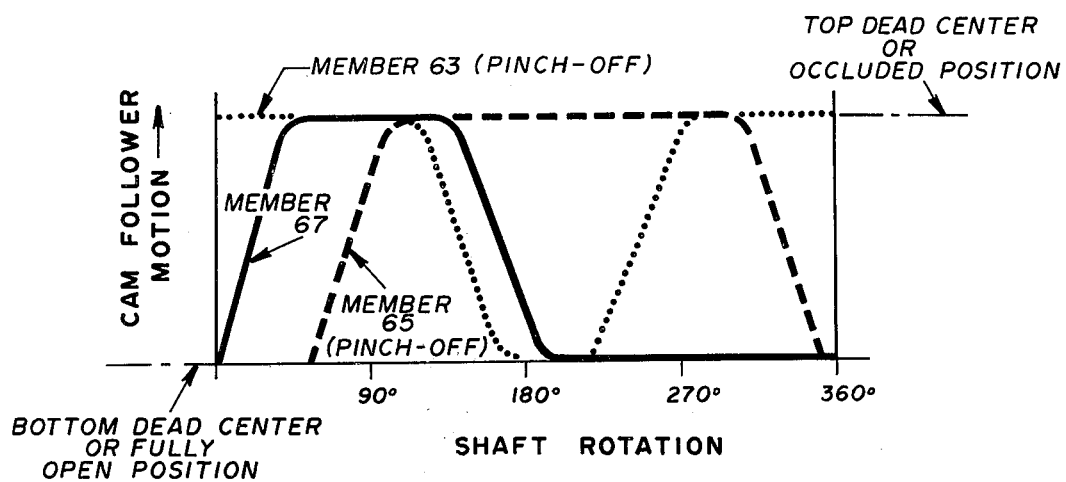
FIG. 5 is a graph illustrating the operation of the cam driving means illustrated in FIG. 3.

Very generally, the medical infusion system of the invention includes (FIG. 1) an upstream portion 11, which may be in fluid communication with a source 12 of fluid. A downstream portion 13 is secured suitably for delivering the fluid or semi-solid to a patient 14. A pump 15 pumps fluid from the upstream portion 11 to the downstream portion 13. The pump includes (FIG. 3) means 16 for supporting a conduit means 17 extending between the upstream and downstream portions. Means 21 are provided for selectively restricting and opening the conduit means 17 at locations spaced therealong in a sequence such as to pump fluid in the conduit means. The conduit means include a replaceable cassette or rigid section 18 forming a rigid enclosure with a window 19 therein. A flexible diaphragm 20 extends across the window and is impermeable to the passage of fluids or semi-solids. Part of the restricting means engage the diaphragm and is given incrementally to control pumping.

Referring now more particularly to FIG. 1, the invention is shown in the form of an intravenous delivery system for delivering fluid from a fluid reservoir or storage means 12 to a patient 14. The fluid is introduced intravenously through a suitable catheter 23 attached to the downstream portion 13 of the delivery system. The catheter is held in place by adhesive tape 25 on the arm of the patient 14 as is well known in the art. The fluid reservoir 12 may be a conventional intravenous delivery system bottle suspended on a stand 27. A drip chamber 29 is attached to the lower portion of the bottle 12 and may be of conventional construction. An empty bottle alarm 31 of suitable design may be employed beneath or attached to the drip chamber to signal when the contents of the bottle 12 have been drained. The contents of the bottle 12 pass through the upstream portion 11 of the delivery system, the upstream portion constituting, in the illustrated embodiment, a flexible hose.

Although the bottle 12 is shown positioned on the support 27 in an elevated condition with respect to the patient 14, as is typical of many intravenous delivery systems, it is not critical in the system of the invention that the bottle be so elevated inasmuch as the fluid is conveyed to the patient by the positive pumping action of the pump 15. The pump 15, shown in FIG. 1, may be suitably contained in a housing 33 having control knobs including a knob 35 thereon and a vent 37 for cooling the internal contents. The pump 15 may be supported on a bedside table 39 or other suitable structure and is located between the upstream portion 11 and the downstream portion 13 of the delivery system. Grommets 41 form the entrance and the exit to the housing 33 for the upstream and downstream portions 11 and 13, respectively.

Referring now more particularly to FIG. 2, the internal construction of a portion of the pump 15 is shown in a schematic perspective drawing. A rigid section 18 of tubing or conduit forms a rigid enclosure or cassette for the pump which is easily replaceable. The rigid section 18 is supported inside the housing 33 of the pump 15 by suitable supporting means, not shown. The upstream portion 11 (FIG. 1) of the system is coupled to the rigid section 18 which is made from a rigid (plastic) material by a suitable sleeve coupling 105. Similarly, the downstream portion 13 (FIG. 1) of the system is coupled to the tube section 18 by a suitable sleeve coupling 107. A window 19 is cut out of the tube section 18 and is of a size such as to permit passage into the tube section 18 through the window of restricting means described below. An outer sleeve 111 of flexible resilient material is fitted over the outside of the tube section 18 covering the window 19. The sleeve 111 is of material which is impermeable to passage of the fluid being infused and thereby provides, over the window 19, a flexible diaphragm 20 through which the restricting means described below can change the volume of the interior of the rigid section 18. The sleeves 105 and 107 are also of flexible material and are positioned in alignment with the restricting means described below.

As previously mentioned, restricting means 21 are employed to sequentially restrict and open the conduit means 17 in a sequence such as to pump fluid in the conduit means from the upstream portion 11 to the downstream portion 13 of the delivery system. Although any suitable means for constricting the conduit means 17 in the manner described below may be employed, in the apparatus illustrated in FIGS. 3 and 4, the restricting means 21 include first, second and third movable members 63, 65, and 67, respectively. The movable member 63 comprises an elongated bar which is slidably supported by suitable means not shown. Similarly, the second movable member 65 comprises an elongated bar slidably mounted by suitable means, not shown. The movable members 63 and 65 have rounded ends for engaging the respective sleeves 105 and 107, and are shaped and sized to conform with a rounded recess in the support means 16, thus ensuring that the sleeves can be completely pinched-off at the two locations where they are engaged by the movable members 63 and 65.

The third movable member 67 comprises an elongated bar slidably mounted in a suitable support, not shown. The member 67 engages the diaphragm 20 over the window 19 in the rigid section or cassette 18. As the member 67 moves forward, the membrane is distended inwardly as shown in FIG. 4, thereby reducing the volume defined by the rigid section 18.

For moving the movable members 63, 65, and 67 in the desired sequence, the ends of the movable members opposite the tube section 19 carry suitable cam followers, not shown, biased resiliently against the surface of respective cams 91, 93, and 95. The cams 91, 93, and 95 are mounted on a cam shaft 97 which is rotated by a driving motor 103. The driving motor is a stepping motor to provide incremental rotation of the shaft and therefore incremental movement and control over the members 63, 65 and 67.

In FIG. 3, the second movable member 65 is in a position such as to restrict or pinch-off the sleeve 107. Due to the natural flow or pressure head of the fluid in the upstream portion, or to the suction (negative pressure) created by the retraction of the member 67, the rigid section 18 fills as far as the movable member 65. The pumping stroke is illustrated in FIG. 4 wherein the movable member 65 is retracted to fully open the sleeve 107 and the first movable member 63 has closed to restrict or occlude the sleeve 105 upstream from the movable member 67. Movement of the movable member 67 inwardly reduces the volume of the rigid section 18 causing at least some of the contents to be expelled toward the downstream portion of the delivery system. The distance which the movable member 67 moves inwardly determines the displacement volume during the pumping stroke. The filling and pumping strokes are conducted in sequence and repeated according to the rotation of the cam shaft 97 and the configuration of the cams 91, 93 and 95.

Referring to FIG. 5, a plot is provided illustrating the motion versus degrees of shaft rotation for the three movable members 63, 65 and 67, respectively. At the left-hand edge position or 0° position shown in the plot, the upstream movable member 63 is closed whereas the members 65 and 67 are open. Movement of the member 67 from the fully open position to the occluded position displaces at least some of the contents of the rigid section 18 between the members 63 and 65. Following this movement, the member 65 moves to the occluded position to close the downstream section of the rigid section 18. Once this occurs, the member 63 moves to the open position as does the member 67, allowing filling of the tube section once again. Between 180° and 270°, the upstream movable member 63 moves from the open position to the closed position, and between 270° and 360° the downstream movable member 65 moves to the open position. This places the system in readiness for the next displacement stroke beginning with 0°.

Figure 6:
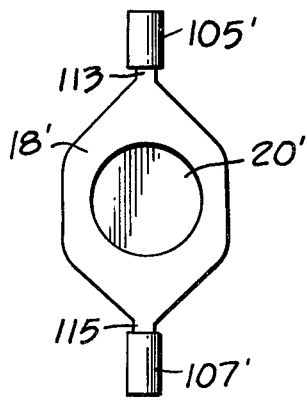
FIG. 6 is a top plan view of an alternate configuration of a cassette and portions of the pump of the system of FIG. 1.
Figure 7:
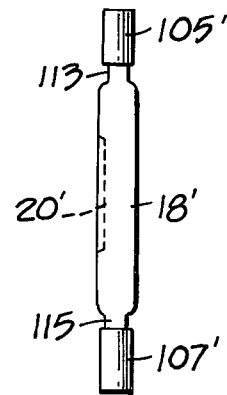
FIG. 7 is a side view of the pump portion of FIG. 6.

Referring now to FIGS. 6 and 7, an alternate configuration for the rigid section or cassette of the pump is shown. The rigid section or rigid enclosure 18 is of a flattened configuration defining a pancake shaped cavity or enclosure. The window 19 is circular and the diaphragm 20' is formed by a membrane spanning the window. The membrane may be formed integrally with the rigid enclosure or part thereof during molding, or may be formed separately and suitably attached. Inlet and outlet orifices 113 and 115 are formed integrally with the rigid section 18', and the flexible sleeves 105' and 107' are attached thereto.

Typical applications of the invention would involve maximum pressures of about 20 psi. Accordingly, the "rigidity" of the rigid section 18 is selected appropriately. It is preferred that the movable member 67 engage the diaphragm 20 throughout its stroke, and that there always be a slight inward loading on the diaphragm. For satisfactory accuracy, it is preferred that the unsupported or unengaged area of the diaphragm not exceed 75% of the total diaphragm (window) area.

Rather than the cam drive illustrated, other means for operating the restricting means may be utilized, such as a lead screw drive. However, incremental control over the diaphragm movement is significant in achieving proper accuracy and control. By suitable design, a desired displacement volume may be selected for each step. Digital control is then readily possible with commercially available and relatively inexpensive microcomputer chips. Functions such as flow rate, total volume delivered and flow error monitoring may easily be handled by known digital techniques.

It is usually preferable to design the system to operate such that the return strokes, i.e. filling strokes, be of the same duration regardless of the delivery rate and volume. Thus, the flow may be more even where the member 67 is retracted at a relatively quick fixed rate as opposed to the varying inward (delivery) rate. Digital capability makes such operation easily achievable.

The size of the outlet and inlet openings relative to the diaphragm or window size is of significance. With inlet and outlet openings which are too large, regurgitation becomes a large enough factor to deleteriously affect accuracy. Thus, it is preferred that each of the inlet and outlet openings have a cross-sectional area having a ratio to the diaphragm or window area of not greater than about 0.3.

The medical infusion system of the invention provides some significant advantages over many prior art constructions. There are no valves employed in the system for the pumping operation and therefore none in the cassette, thus significantly improving the reliability and reducing the complexity of manufacture and therefore the cost. Any reasonably strong type of flexible tubing will operate as the sleeves 105 and 107 in the system of the invention, and the tubing may be easily replaced since it is inexpensive. By properly designing the cams and the size of the movable restricting elements, good constant flow rates may be achieved, even to very low rates.

Various modifications of the invention in addition to those shown and described herein will become apparent to those skilled in the art from the foregoing description and accompanying drawings. Such modifications are intended to fall within the scope of the appended claims.

What is claimed is:

1. A pump for use in a medical infusion system for pumping fluid or semi-solids from an upstream portion of the infusion system to a downstream portion thereof, said pump comprising, conduit means, means for supporting said conduit means for extending between the upstream and downstream portions of the system, first constricting means for selectively restricting and opening said conduit means at a first location thereof, second restricting means for selectively restricting and opening said conduit means at a second location thereof spaced from said first location, third restricting means for selectively restricting and opening said conduit means at a third location thereof between said first and second restricting means to displace a predetermined volume in said conduit means, and means for operating said first, second and third restricting means in a sequence such as to pump fluids or semi-solids in said conduit means, said conduit means including a rigid section positioned between said first and second locations and defining a pumping cavity, said rigid section having a window therein, a flexible diaphragm extending across said window and being impermeable to the passage of fluid or semisolids therethrough, said third restricting means being engaged with said diaphragm, said operating means including drive means for providing incremental movement of said third restricting means to control incrementally the pumping of fluids or semi-solids said rigid section of said conduit means being of substantially tubular configuration, said diaphragm being formed in part by a relatively flexible sleeve positioned coaxially of said rigid section and extending over said window therein whereby said diaphragm comprises the portion of said flexible sleeve extending over said window.

2. A pump according to claim 1 wherein said supporting means include means defining an elongated groove for receiving the flexible conduit.

3. A pump according to claim 1 wherein said first and second locations on said conduit means each includes a flexible tube connected to said rigid section of said conduit means.

* * * * *